(12) United States Patent
Khanmamedova

(10) Patent No.: US 6,420,308 B1
(45) Date of Patent: Jul. 16, 2002

(54) HIGHLY SELECTIVE SHELL IMPREGNATED CATALYST OF IMPROVED SPACE TIME YIELD FOR PRODUCTION OF VINYL ACETATE

(75) Inventor: Alla Konstantin Khanmamedova, Houston, TX (US)

(73) Assignee: Saudi Basic Industries Corp, Riyadh (SA)

(*) Notice: Subject to any disclaimer, the term of this patent is extended or adjusted under 35 U.S.C. 154(b) by 5 days.

(21) Appl. No.: 09/612,159

(22) Filed: Jul. 7, 2000

(51) Int. Cl.⁷ .......................... B01J 23/02; B01J 23/04; B01J 31/00; B01J 27/06; C07C 69/02; C07C 67/05

(52) U.S. Cl. .................. 502/344; 502/157; 502/170; 502/171; 502/224; 502/230; 502/258; 502/344; 502/243; 560/231; 560/245; 560/247; 560/261

(58) Field of Search ................ 560/245, 231, 560/247, 261; 502/170, 230, 243, 157, 171, 224, 258, 344

(56) References Cited

U.S. PATENT DOCUMENTS

| | | | |
|---|---|---|---|
| 4,048,096 A | * 9/1977 | Bissot et al. | |
| 4,370,492 A | 1/1983 | Wunder et al. | 560/245 |
| 5,179,056 A | 1/1993 | Bartley | 502/170 |
| 5,189,004 A | * 2/1993 | Bartley | |
| 5,225,388 A | 7/1993 | Wunder et al. | 502/170 |
| 5,274,181 A | 12/1993 | Bartley et al. | 560/245 |
| 5,314,858 A | 5/1994 | Colling | 502/330 |
| 5,332,710 A | 7/1994 | Nicolau et al. | 502/243 |
| 5,342,987 A | 8/1994 | Bartley | 560/245 |
| 5,559,071 A | 9/1996 | Abel et al. | 502/326 |
| 5,567,839 A | 10/1996 | Gulliver et al. | 560/245 |
| 5,693,586 A | 12/1997 | Nicolau et al. | 502/330 |
| 5,808,136 A | 9/1998 | Tacke et al. | 560/243 |
| 5,854,171 A | 12/1998 | Nicolau et al. | |
| 5,968,860 A | 10/1999 | Herzog | |
| 5,972,824 A | 10/1999 | Herzog et al. | |
| 6,015,769 A | 1/2000 | Wang | |
| 6,017,847 A | 1/2000 | Wang | |

OTHER PUBLICATIONS

CRX Handbook of chemistry and Physics, 62nd edition, 1981–1982, p. F–108.*

* cited by examiner

Primary Examiner—Paul J. Killos
Assistant Examiner—Farhad Forohar
(74) Attorney, Agent, or Firm—Charles M. Cox; Jim D. Wheelington

(57) ABSTRACT

A shell impregnated catalyst of Pd—Au produced on a silica support to have a Pd loading of 1.8 g/L of catalyst to about 7.2 g/L and a Au to Pd weight ratio of 0.3 to 2.0 by impregnating the support with aqueous solutions of palladium and gold salts or acids and thereafter precipitating water insoluble compounds of Pd and Au on the with alkali metal silicate or hydroxide solutions, then dried, and the surface precipitated compounds of Pd and Au are then reduced by reaction with ethylene or hydrogen at a temperature of greater than 150° C. up to 310° C. or with hydrogen up to 299° C. until substantially all of the Pd and Au contents are reduced to a free metal state, after which the support is impregnated with potassium acetate to an extent of 6 to 7 weight percent of the weight of the total catalyst. For production of vinyl acetate (VA) such catalyst has a space-time yield (STY) and specific activity (SA) about 20–30% greater than an otherwise identical catalyst composition that is formed from impregnated support reduced at 150° C., and in a temperature range of 140° C. to 160° C. at a gas hourly space velocity of 4500/hr will at 120 psig exhibit a VA selectivity of 90% or greater when operated under reaction conditions that result in a STY of at least 600.

21 Claims, No Drawings

HIGHLY SELECTIVE SHELL IMPREGNATED CATALYST OF IMPROVED SPACE TIME YIELD FOR PRODUCTION OF VINYL ACETATE

CROSS-REFERENCE TO RELATED APPLICATIONS

Not applicable.

STATEMENT REGARDING FEDERALLY SPONSORED RESEARCH

Not applicable.

BACKGROUND OF THE INVENTION

1. Field of the Invention

This invention relates to shelled Pd—Au catalyst of particular characteristics, and methods for their production, which are effective for catalyzing the vapor phase reaction of an alkene (such as ethylene) with an alkanoic acid (such as acetic acid) and oxygen to produce an alkenyl alkanoate (such as vinyl acetate) at high values for space-time yield, specific activity, and with a high selectivity for conversion of the alkene to the alkenyl alkanoate (such as ethylene to vinyl acetate).

2. Description of the Related Art

Vinyl acetate (VA) is a commodity chemical in high demand as a monomer for production of poly(vinyl acetate). This important polymer, and its derivatives, finds extensive uses as adhesives, paints and other coatings, films and laminating materials. Many techniques have been reported in the prior art for the production of VA. A chief technique is a catalyzed gas phase reaction of ethylene with acetic acid and oxygen. Today a type of catalyst widely use for this reaction is a surface shell impregnated catalyst of a type as described in U.S. Pat. No. 4,048,096 by T. C. Bissot.

Bissot's U.S. Pat. No. 4,048,096 discloses a catalyst having a specific activity of at least about 83 grams of vinyl acetate per gram of precious metal ( Pd+Au ) per hour measured at 150° C. and a reaction pressure of 120 psig. The catalyst consists of: (1) catalyst support particles having a particle diameter of from about 3 to about 7 mm and a pore volume of from about 0.2 to about 1.5 ml/g, (2) palladium and gold distributed in a surface layer of the catalyst support extending less than about 0.5 mm into the support, the palladium being present in an amount of from about 1.5 to about 5.0 grams per liter of catalyst, and the gold being present in an amount of from about 0.5 to about 2.25 grams per liter of catalyst, and (3) from about 5 to about 60 grams per liter of catalyst of an alkali metal acetate. Palladium is the active catalyst metal and the gold is a catalyst promoter.

The Bissot '096 patent process for catalyst preparation comprises: (1) impregnating the catalyst support with an aqueous solution of water-soluble palladium and gold compounds, (2) precipitating water-insoluble palladium and gold compounds on the catalyst support surface by contacting the impregnated catalyst support with a solution of compounds (preferably sodium metasilicate) capable of reacting with the water-soluble palladium and gold compounds to form water-insoluble palladium and gold compounds, (3) converting the water-insoluble palladium and gold compounds into palladium and gold metal on the support surface by treatment with a reducing agent, (4) washing the catalyst with water, (5) drying the catalyst, (6) impregnating the catalyst with an alkali metal acetate promoter (e.g., a potassium promoter), and (7) drying the catalyst.

The improvement disclosed in Bissot '096, as compared to prior Pd—Au supported catalysts, involves distributing the catalyst loading of palladium and gold as a surface layer on the catalyst support which is less than about 0.5 millimeter into the support from its surface. The impregnating step is carried out with an aqueous solution of palladium and gold compounds and the total volume of the solution is from about 95 to about 100% of the absorptive capacity of the catalyst support. The precipitating step in Bissot is carried out by soaking the wet catalyst support with a solution of an alkali metal silicate, the amount of alkali silicate being such that, after the alkali metal silicate solution has been in contact with the catalyst support for about 12 to 24 hours, the pH of said solution is from about 6.5 to about 9.5. In all examples of Bissot the reduction of the precipitated compounds to Pd and Au metals is accomplished by reaction with a hydrazine solution.

As is apparent from a reading of the Bissot patent, a major concern in this art of vinyl acetate (VA) production has always been to improve the space-time yield (STY) and also the specific activity (SA) of the catalysts. Since the description of this shell type of catalyst by Bissot others have attempted to improve the catalyst in respect to its space-time yield, specific activity, and/or its selectivity.

In U.S. Pat. Nos. 5,179,056; 5,189,004; and 5,342,987 by W. J. Barley it is reported that a shell impregnated catalysts of the Bissot type is improved in respect to its STY if it is essentially free of sodium; such as if it prepared from ingredients that are essentially free of sodium as per the '056 patent, or if its sodium content is removed by washing with water or an aqueous solution of a potassium promoter as in the '004 patent, or by washing the catalyst at an intermediate stage of its production with an ion exchange solution as in the '987 patent. In all of the above patents the exemplified catalyst are reduced with hydrazine solutions. U.S. Pat. No. 5,693,586 reports that a shell impregnated catalysts of the Bissot type which are made from reagents that are all potassium salt compounds are of an improved carbon dioxide selectivity. In this patent all example catalyst are reduced with ethylene at a temperature of 150° C.

Barley et al. in U.S. Pat. No. 5,274,181 reports that a shell impregnated catalysts of the Bissot type is improved in respect to its STY if it is prepared to have, at a Pd loading of 2.5 g/L (0.33 wt %) to 6.1 g/L (1.05 wt %), a weight ratio of Au to Pd in the range of 0.6 to 1.25. All catalyst examples of this patent are reduced by reaction with a hydrazine solution.

U.S. Pat. No. 5,567,839 reports that a shell impregnated catalysts of the Bissot type is improved in respect to its STY if a barium salt rather than a sodium silicate is use to precipitate the Pd and Au compounds into the shell. All catalyst examples of this patent are reduced by reaction with a hydrazine solution.

The selectivity of a palladium-gold catalyst in vinyl acetate synthesis also is influenced by the extent and uniformity of the palladium metal and gold metal distribution on the exterior and/or interior surfaces of a porous catalyst support substrate, such as carbon dioxide selectivity and oxygen conversion in an ethylene, acetic acid and oxygen vapor phase reaction.

Attempts to provide a uniform distribution of the palladium and gold metals on the catalyst support has involved manipulation of the catalyst preparation steps and/or by using support substrates having various specified pore dimensions. Particularly useful improvements in preparing highly active catalysts for vinyl acetate production are disclosed in U.S. Pat. No. 5,314,858 and U.S. Pat. No. 5,332,710. These references describe process embodiments for improving palladium and gold distribution on a support by manipulating the precipitation step in which the water-soluble precious metal compounds are fixed to the support surface as water-insoluble compounds. In U.S. Pat. No. 5,314,858, fixing precious metals on the support is achieved utilizing two separate precipitation stages to avoid using large excesses of fixing agent. U.S. Pat. No. 5,332,710 describes fixing the precious metals by physically rotating an impregnated catalyst support while the impregnated support is immersed in a reaction solution at least during the initial precipitation period. The rotation immersion procedure yields catalysts in which the metals precipitated on the carrier are said to be more evenly distributed in a thin shell on the support surface. All catalyst examples of these patents are reduced with ethylene at a temperature of 150° C.

Despite such improvements as have been made there is a continuing interest in the development of catalyst compositions that exhibit an even further improved combination of properties for the production of vinyl acetate.

SUMMARY OF THE INVENTION

This invention relates to a shell impregnated catalyst of Pd—Au, and methods for their production, which are effective for catalyzing the vapor phase reaction of ethylene with acetic acid and oxygen to produce vinyl acetate at high values for space-time yield, specific activity, and with a high selectivity for conversion of ethylene to vinyl acetate.

The shell impregnated catalyst of Pd—Au are produced on a silica support to have a Pd loading of 1.8 to about 7.2 g/L of catalyst and a Au to Pd weight ratio of 0.3 to 2.0 by impregnating the support with aqueous solutions of palladium and gold salts or acids, which preferably are high purity potassium tetrachlorpalladate (99.99%) and hydrogentetrachlorauate (99.998%), and thereafter precipitating water insoluble compounds of Pd and Au on the support surface by reaction of the impregnated support with solutions using alkali metal metasilicates or alkali metal hydroxides or mixtures thereof as precipitating agents, preferably a sodium metasilicate solution is used as a precipitating agent in a quantity that exceeds the theoretical amount required to neutralize the Pd and Au salts. The excess of fixing agent depends on volume of fixing solution and acidity of support.

The impregnated support is then washed with deionized water until the final decant is negative to a silver nitrate test, after which it is dried for water removal. The dried support with its surface precipitated compounds of Pd and Au is then reacted with ethylene or hydrogen at a temperature greater than 150° C. and for ethylene up to 310° C. and for hydrogen up to 299° C., preferably for 10 minutes to one hour at a temperature of from 250° C. to 325° C. for ethylene and from 250° C. to 299° C. for hydrogen, until substantially all of its content of Pd and Au are reduced to their free metal state, after which the support is impregnated with potassium acetate to an extent of 6 to 7 weight percent of the total catalyst weight on a dry basis. Thereafter the catalyst is dried.

A catalyst as described above has a space-time yield (STY) and specific activity (SA) about 20–30% greater than an otherwise identical catalyst composition that is reduced with ethylene or hydrogen at 150° C. In a temperature range of 140° C. to 160° C. at a gas hourly space velocity of 4500/hr the catalyst will exhibit a vinyl acetate selectivity of 90% or greater when operated under reaction conditions that result in a STY of at least 600 gVA/L catalyst/hr. Further, such catalysts have a long operational life.

DETAILED DESCRIPTION OF INVENTION

This invention comprises a catalyst for the promotion of a gas phase reaction of an alkene, an alkanoic acid, and an oxygen-containing gas to produce an alkenyl alkanoate. The catalyst is particularly desirable for the gas phase reaction of an ethylene, an acetic acid, and an oxygen-containing gas to produce vinyl acetate.

In the catalyzed gas phase reaction process, ethylene reacts exothermically with acetic acid and oxygen in the vapor phase over a heterogeneous Pd—Au shelled catalysts, giving vinyl acetate and water:

$$CH_2=CH_2+CH_3CO_2H+\tfrac{1}{2}O_2 \rightarrow CH_3CO_2CH=CH_2+H_2O,$$

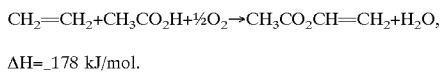

The vinyl acetate reaction process may typically operate at 140–180° C., 5–10 atmospheres (atm), and a gas hourly space velocity (GHSV) of ~4500 h⁻. This will give 8–10% ethylene and 15–40% acetic acid conversion. Oxygen conversion can be up to 90%, and the yields are up to 99% and 94% based on acetic acid and ethylene, respectively.

Reaction temperatures may be between 140° C. and 200° C. Generally the preferred reaction temperature range is 140° C. to 180° C. with 140–160° C. being most preferred. At temperatures below 140° C., the reaction rate is low and it is difficult to keep the acetic acid in the vapor phase. Above 180° C., for a given catalyst, more and more of the ethylene and acetic acid feeds are converted to by products. The principal by product is carbon dioxide. Generally, the other by-products, acetaldehyde, and ethyl acetate are formed at about 1% or less.

Reaction pressures are between 70–200 psig. Typically, the pressure used in commercial plants is 100–150 psig. Higher pressures make it difficult to keep the acetic acid in the vapor phase whereas pressures lower than 70 psig too greatly reduce the STY of the reaction.

The total volume of reaction gases as a gas hourly space velocity (GHSV) is about 3000–5000 STP liter/liter of catalyst per hour. Higher GHSV values result in higher STY and SA values without significantly lowering the selective values for production of vinyl acetate. Therefore, higher GHSV values, such 4500, are preferred. The composition of the reaction gases in volume % is in the range of ethylene, 27–60%; inerts 15–55%; acetic acid 12–17% and oxygen 6–8%. The reaction is operated with a large excess of ethylene and acetic acid. The main reason for doing so is to avoid formation of potentially flammable/explosive mixtures. Oxygen levels above about 9% are not used in order to avoid explosive mixtures. The preferred ranges, respectively are ethylene 50–60%, inerts 20–50%, acetic acid 12–15%, and oxygen 6–7%. Commercially, oxygen is often used in place of air and the percentage of ethylene in the feed is raised.

The support particles used in the process of producing catalyst of this invention are solid particulate materials that are capable of being impregnated with palladium, gold and a potassium promoter and that are inert under the conditions used to produce alkenyl alkanoates, such as vinyl acetate. Illustrative of such support particles are particulate silica, alumina, and silica-aluminas. Silica is the preferred support. The support preferably has a surface area from 100 to 800 square meters per gram. Silica beads of an average diameter of 5 to 6 mm, a surface area of 150 to 200 square meters per gram and a pore volume of 0.6 to 0.7 ml/g, such as "KA-160" sold by Sud Chemie AG, is an example of a most preferred support material.

The aqueous solutions of water-soluble palladium and gold compounds used in the process of this invention may include aqueous solutions of any suitable palladium or gold compound such as palladium (II) chloride, alkali earth metal tetrachloropalladium (II), palladium (II) nitrate, palladium (II) sulfate, gold (II) chloride or auric (III) acid ($HAuCl_4$). However, compounds containing sodium are less preferred and the preferred compounds are potassium tetrachlorpalladate and hydrogentetrachlorauate. Then, for obtaining a high value for the space-time yield (STY) and specific activity (SA) of the catalyst it is preferred to utilize these preferred compounds in their high purity form, meaning 99.9+% purity, preferably 99.99%. Hence, it is preferred to use a potassium tetrachloropalladium of 99.99% purity and hydrogentetrachlorauate of 99.998% purity.

The quantity of Pd and Au compounds to be employed is such as to provide in the final catalyst a Pd loading of from about 1.8 g/L to about 7.2 g/L and a Au loading that places Au in the catalyst in a weight ratio to Pd in the range 0.3 to 2.0. Preferably the quantity of Pd loaded in the catalyst is such to provide the catalyst with a specific activity of greater than 200 g VA/g Pd/hr when operated under reaction conditions of 120 psig and within a temperature range of about 140° C. to about 1600 C that provide a STY of at least about 600 gVA/L cat/hr. The lower is the Pd loading that can be used to obtain the requisite STY values the higher will be the selectivity of conversion to VA, hence Pd loadings in a range of about 3.0 g/L to about 5.4 g/L are preferred.

The support is impregnated in a process designated as "rotation immersion to a point of incipient wetness." The volume of the impregnation solution preferably corresponds to from 95 to 100% (more preferably from 98 to 99%) of the pore volume of the support. In this process, the catalysts support is immersed in the Pd—Au impregnation solution and tumbled or rotated therein during the initial stages of the impregnation of the support with the soluble precious metal compounds. The rotation or tumbling of the supports in the solution should proceed for at least 15 minutes and, preferably, for at least 30 minutes until all of the solution is absorbed. The rotation can last as long as up to 2 hours after which the support may be left without rotation inside the sealed container for one or two hours to complete distribution of the impregnation solution inside the support pores.

Any type of rotation or tumbling equipment can be used as the exact apparatus utilized is not critical. However the extent of the rotating motion may be critical. The rotation should be fast enough so that all surfaces of the impregnated supports are evenly contacted with the impregnation solution as soon as possible. The rotation should not be so harsh that actual abrasion of the support particles takes place. Generally, the extent of rotation should be about 1 to 30 rpm and possibly even higher especially in the beginning of rotation depending upon the exact support utilized, the amount of support and the amount of precious metal to be impregnated into the support. The rpm to be used is variable and may also depend upon the apparatus utilized, the size and shape of the support, the type of support, and metal loading.

The precipitating agents used in the process of the present invention catalysts include sodium, lithium and potassium silicates and hydroxides. It is preferred to use sodium metasilicate as the precipitating agent. The precipitating agents are preferably employed in the form of aqueous solutions containing a 1.1 to 2.5 molar excess of the precipitating agents depending on support acidity and volume of used solution. The volume of such solutions used is preferably just sufficient to cover the support particles. The impregnated support is immersed into the fixing solution and allowed to remain completely covered (for 1 day up to about 3 days (~70 hours)) at room temperature until a final pH value of 6.5–8.8 is attained. The exact quantity of alkali, time of fixing and final pH is dependent on the alkali type, the acidity of the support, and the quantities of precious metals used.

After fixation is completed the impregnated support beads are then removed from fixing solution and rinsed with deionized (D.I.) water. Further washing may then done in a batch or a continuous mode. Further washing at room temperature should continue until the decant wash water content of chlorine ions is below 100 ppm, wherein the final decant gives a negative result to a silver nitrate test.

After washing is complete the impregnated support beads are dried, such as at 90–150° C. in a forced air or nitrogen oven.

The reducing agent used in the process of this invention is ethylene or hydrogen to which the dried impregnated support are exposed while at a temperature greater than 150° C. and up to 310° C. for ethylene and up to 299° C. for hydrogen, preferably of or greater than 200° C. and more preferably to a temperature greater than 250° C. such as a range of 275° to 310° C. for ethylene and 2750 C to 299° C. for hydrogen, and most preferably at 300° C. for ethylene and 299° C. for hydrogen, for a time sufficient to complete the reduction of Pd and Au to their free metal state. Generally, the reduction is carried out for no longer than five hours, and preferably less than one hour, preferably about 10 to 60 minutes.

Reduction of the impregnated support at these high temperatures has been found to significantly increase the activity of the catalyst as compared to catalyst synthesized from impregnated support that are reduced at lower temperatures such as 150° C. as has typically heretofore been use in an ethylene or hydrogen reduction step. The higher reduction temperatures increase the STY of the catalyst by about 20–30% compared to one formed from impregnated support reduced at 150° C. Thus, for catalyst compositions that are otherwise identical and of a calculated 0.6 wt. % Pd loading and a calculated 0.5% wt. Au loading and operated to provide a STY of 600 g VA/L cat/hr, the catalyst synthesized from impregnated support reduced at 300° C. can be operated at a 8–10° C. lower reaction temperature wherein the selectivity for conversion to vinyl acetate is 92–93% rather than the 90% range of one reduced at 150° C.

For purposes of their reduction the impregnated support beads may first be heated in a flow of an inert gas, such as a nitrogen flow, from room temperature to 150° C. The impregnated support may then be held in the inert gas flow at 150° C. for 0.5–1 hour. Adsorbed water evolves during this heating period. The temperature may then be raised to 299–300° C. Then the inert gas flow may be maintained and a volume of ethylene or hydrogen (1–5% by volume, preferably) may be introduced into the inert gas flow to form the reducing gas mixture to which the catalyst beads are exposed.

For purpose of their reduction dried impregnated beads may be directly placed into heater at 300° C. with an ethylene-inert or 299° C. with a hydrogen-inert gas flow mixture. Reducing gas flow has to be sufficient to provide complete reduction of the catalyst metals and may be varied in contact time range.

After about 10–15 minutes to about 5 hours of reduction in the gas mixture, the 1–5% ethylene or hydrogen in inert gas mixture may be turned off leaving the pure inert gas flow, and the beads may then be cooled back to room temperature. Shorter reduction times yield catalysts of higher STY values; hence shorter reduction times of from about 15 minutes to about 1 hour are preferred. Hydrogen is the preferred reducing gas.

The potassium promoters used in the process of this invention for producing the catalysts may include potassium alkanoates and any potassium compound that is converted to a potassium alkanoate during the alkenyl alkanoate-forming reaction (i.e., the reaction of ethylene, an alkanoic acid and an oxygen-containing gas in the presence of the catalyst to produce a alkenyl alkanoate). Potassium acetate is preferred as the promoter and is preferably added to the extent of about 5–10 wt. %, of the total catalyst weight on a dry basis. The promoter is preferably applied in the form of aqueous solutions. It is preferred to accomplish placement of the promoter on the reduced impregnated support beads by the "rotation immersion to a point of incipient wetness" technique as previously described.

The catalyst is dried to remove water.

EXAMPLES

Catalyst Preparation

Unless otherwise indicated, in all of the examples to follow the raw materials used for production of catalyst are as follows:

Support: KA-160; Gold: Hydrogen tetrachloroaurate (III) trihydrate, Palladium: Potassium or sodium tetrachloropalladate (II), 99.99%; Fixing agent: Sodium metasilicate, anhydrous: sodium hydroxide; potassium hydroxide; Promoter: Potassium acetate; Water: Deionized water (D.I.), ~18 megohm-cm resistance; Reducing Agent: 5% ethylene in nitrogen or 5% hydrogen in nitrogen, as indicated.

Unless otherwise indicated, in all of the examples to follow the synthesis procedure for preparation of 1 L of catalyst is given below. When palladium sources other than potassium tetrachloropalladate or fixing agents other than sodium metasilicate were used, the quantities of the palladium salt or the fixing agent were adjusted to obtain the correct molar ratios.

1. Impregnation step.

A solution of 6.90 g of $HAuCl_4 \cdot 3H_2O$ and 12.70 g of $K_2PdCl_4$ in 360 ml of DI water was used to impregnate 600 g (1 L) of KA-160 at room temperature (R.T.) by an incipient wetness technique. The KA-160 was placed in a two-liter round bottom flask. After pouring the solution over the KA-160, the flask was connected to a rotary evaporator. The flask was then rotated for 5–10 minutes until all the solution was adsorbed by the support. After this, rotation was stopped and the impregnated support was left undisturbed for at least 1 hour. During that time the flask with impregnated support was stoppered to prevent solution evaporation from the surface of support.

2. Fixing step.

For preparation of a 0.125 M $Na_2SiO_3$ fixing solution, 18.30 g of $Na_2SiO_3$ was dissolved in 1200 ml of D.I. water (pH~13.0).

The impregnated support from step 1 was reacted with the fixing solution by rapidly pouring the fixing solution over the beads. The fixing solution completely covered the beads. The fixing reaction was allowed to proceed for 3 days (~70 hours) at room temperature to a final pH value of 8.0–8.5.

3. Washing step.

The beads were then removed from fixing solution and rinsed with about 4 L of D.I. water. Further washing was then done in a batch mode. For further washing, a total of at least 200 L of D.I. water were used. The impregnated support were immersed into 40 L of water at room temperature. The water layer above the beads was gently stirred overnight. The wash water was decanted the next day and replaced with another 40 L portion of water. The washing/decanting procedure was carried out 5 times to decrease content of chlorine ions to below 100 ppm, wherein the final decant gives a negative result to a silver nitrate test.

4. Drying step.

The impregnated support were then dried overnight at 90–100° C. in a forced air oven.

5. Reduction step.

The reduction procedure was carried out in a glass or quartz tube heated with a tube furnace.

The impregnated support heated in a nitrogen flow (rate 300–330 ml/min) from room temperature to 150° C. at a rate of 5° C./min. The beads were then held in the nitrogen flow at 150° C. for 1 hour. Adsorbed water evolved during this heating period. The temperature was then raised at a rate of 1.5° C./min to 300° C. for ethylene or to 299° C. for hydrogen. Then the nitrogen flow was maintained and a 5% volume of reducing gas (either ethylene or hydrogen, ethylene for examples 1–12 and hydrogen for example 13) in nitrogen mixture was introduced at a flow of 300–330 ml/min. After 5 hours of reduction (varied times for example 13), the 5% ethylene (or hydrogen in example 13) in nitrogen mixture was turned off leaving the pure nitrogen flow. The beads were then cooled to room temperature under nitrogen.

6. Promoting step.

Reduced impregnated support was promoted with 6–7 wt. % of potassium acetate (KOAc). A solution of 39.2–45.8 g of KOAc in 360 ml of D.I. water was used to impregnate the beads by the rotation immersion to a point of incipient wetness mode. Beads were placed into a flask.

7. Final drying step.

The catalyst was dried at 90–100° C. overnight in a forced air oven.

Catalyst Reactions

Unless otherwise indicated, in all of the examples to follow the reactor and catalysts conditions were as follows:
Reactor A micro reactor unit built by Zeton Altamira was used for screening catalysts and was designed for attended operations. Gases were fed through a Brooks mass flow meters and acetic acid was fed by an ISCO syringe pump. Controls were manually operated. The unit was interfaced with an on line GC.

A reactor tube of ¾ inch diameter was used so the catalyst pellets could be inserted. Catalyst loading was typically 2.5 grams along with 37.5 grams of 5-mm glass beads as a diluent. All catalysts consist of a commercial silica type support; KA-160 marketed by Sud Chemie. The active component is palladium. Generally another metal, gold, and a promoter, potassium acetate are added to the catalyst. The catalysts are of the shell type in which the metals are located within the first 0.30–0.35 mm of the 5-mm spheres.
Temperatures Reactions were carried out at three different temperatures ranging between 135 and 170° C. Thereafter for the STY values herein reported a least squares Arrhenius curve was calculated based upon the data points and the 140° C., 150° C., and 160° C. values for STY were determined and are reported in the table of results below. Likewise the selectivity of conversion to vinyl acetate (VA) were measured at the three temperatures and a polynomial curve was calculated and the selectivity values at 140° C., 150° C., and 160° C. were determined and are reported in the table of results below. The principal by product was carbon dioxide. Generally, the other by products, acetaldehyde and ethyl acetate were formed at about 1% or less.

Pressures

Reaction pressures were either 120 psig or 50 psig as reported in the table of results below. Typically, pressure used in commercial plants is 100–150 psig. Some runs with the catalyst of this invention were conducted at a reaction pressure of 120 psig. High performing catalysts are better compared in the lab at 50 psig due to mass transport problems at 120 psig. Pressure was maintained at 50 psig for a latter series of runs. The STY of a catalyst at 50 psig of pressure was found to be about one half the value of that catalyst when run at 120 psig.

Flow Rates

The total volume (GHSV) of reaction gases was maintained at 4,500 STP liter/liter of catalyst per hour. Initial volume % used in these examples are 55% $C_2H_4$, 26.0% He, 12.5% acetic acid and 6.5% $O_2$. Oxygen in these examples is introduced as a 20% oxygen-80% helium blend. For the evaluation of 2.5 grams of whole beads, the flow rates were: ethylene 179 standard cubic centimeters (sccm), 20% $O_2$ 106 sccm, and acetic acid 40.75 sccm. Gas flow rates were controlled and measured by Brooks mass flow controllers with ranges of 0–500 sccm.

Acetic acid was fed as a liquid and flow rate was controlled by an ISCO pump that can give a minimum flow rate of 0.1 μl/min (liquid). The acetic acid liquid was vaporized by introducing it into a mixing tee at 150° C. along with the ethylene and $O_2$/He. The acetic acid (vapor) and other gases were then mixed in a static in line mixer before entering the reactor.

Flammability

Flammability limits of the ethylene and oxygen mixture depend on temperature, pressure, and composition. It is shifted by additional components, such as acetic acid, and helium. In general, the oxygen concentration at the entry to the reactor is ≦9 vol. %, based on acetic acid free mixture. A PLC computer utilizing electrical output from the mass flow meters was used to prevent the formation of flammable ethylene oxygen mixtures.

TABLE OF CATALYST RESULTS[1,2]

| Example No. | Source | Pd Calc. (Actual) | Au Calc. (Actual) | Temp. ° C. | Reaction Pressure (PSIG) | Reaction Temp. ° C. | VA Selectivity (%) | Space Time Yield |
|---|---|---|---|---|---|---|---|---|
| 1. (SMS) | 99.998% $Na_2PdCl_4$ | 0.63 (0.59) | 0.52 (0.26) | 150 | 120 | 140 150 160 | 94.7 92.4 89.5 | 220 322 470 |
| 2. (SMS) | 99% $K_2PdCl_4$ | 0.63 (0.56) | 0.52 (0.26) | 150 | 120 | 140 150 160 | 94.6 93.1 90.2 | 205 320 495 |
| 3. (SMS) | 99.99% $K_2PdCl_4$ | 0.63 (0.54) | 0.52 (0.39) | 150 | 120 | 140 150 160 | 94.7 93.4 91.2 | 280 385 530 |
| 4. (KOH) | 99.99% $K_2PdCl_4$ | 0.63 (0.54) | 0.52 (0.36) | 150 | 120 | 140 150 160 | 94.2 92.2 90.2 | 288 394 500 |
| 5. (NaOH) | 99.99% $K_2PdCl_4$ | 0.63 (0.54) | 0.52 (0.28) | 150 | 120 | 140 150 160 | 94.3 93.3 91.2 | 270 378 528 |
| 5a. (NaOH) | 99.99% $K_2PdCl_4$ | 0.63 (0.54) | 0.52 (0.28) | 300 | 120 | 140 150 160 | 95.2 93.8 91.3 | 320 420 555 |
| 6. (SMS) | 98% $Na_2PdCl_4$ | 0.63 (0.63) | 0.52 (0.25) | 150 | 120 | 140 150 160 | 94.7 92.8 90.9 | 193 309 425 |
| 7. (SMS) | 98% $NA_2PdCl_4$ | 0.63 (NA) | 0.52 (NA) | 300 | 120 | 140 150 160 | 94.7 91.9 89.1 | 265 391 516 |
| 7a. (SMS) | 98% $Na_2PdCl_4$ | 0.63 (NA) | 0.52 (NA) | 500 | 120 | 140 150 160 | 0 0 0 | 0 0 0 |
| 8. (SMS) | 99.99% $K_2PdCl_4$ | 0.63 (0.71) | 2.4 (0.86) | 150 | 120 | 140 150 160 | 92.6 92.3 90.9 | 455 500 560 |
| 8a. (SMS) | 99.99% $K_2PdCl_4$ | 0.63 (0.71) | 2.4 (0.86) | 150 | 50 | 140 150 160 | 94.6 93.3 91.7 | 216 270 340 |
| 9. (SMS) | 99.99% $K_2PdCl_4$ | 0.63 (0.58) | 0.52 (0.36) | 150 | 120 | 140 150 160 | 94.4 92.4 90.0 | 300 430 610 |
| 9a. (SMS) | 99.99% $K_2PdCl_4$ | 0.63 (0.58) | 0.52 (0.36) | 150 | 50 | 140 150 160 | 94.5 93.4 90.2 | 150 220 310 |
| 10. (SMS) | 99.99% $K_2PdCl_4$ | 0.63 (0.63) | 0.52 (0.42) | 150 | 50 | 140 150 160 | 94.8 93.1 91.3 | 185 252 343 |
| 10a. (SMS) | 99.99% $K_2PdCl_4$ | 0.63 (0.63) | 0.52 (0.42) | 300 | 50 | 140 150 | 94.3 92.6 | 260 321 |

-continued

TABLE OF CATALYST RESULTS[1,2]

| Example No. | Source | Pd Calc. (Actual) | Au Calc. (Actual) | Temp. ° C. | Reaction Pressure (PSIG) | Reaction Temp. ° C. | VA Selectivity (%) | Space Time Yield |
|---|---|---|---|---|---|---|---|---|
| | | | | | | 160 | 90.0 | 413 |
| 10b. (SMS) | 99.99% K$_2$PdCl$_4$ | 0.63 (0.63) | 0.52 (0.42) | 350 | 50 | 140 | 93.6 | 49 |
| | | | | | | 150 | 92.9 | 98 |
| | | | | | | 160 | 91.0 | 176 |
| 11. (SMS) | 99.99% K$_2$PdCl$_4$ | 0.63 (0.58) | 0.52 (0.39) | 150 | 50 | 140 | 95.2 | 165 |
| | | | | | | 150 | 93.9 | 230 |
| | | | | | | 160 | 91.4 | 320 |
| 11a. (SMS) | 99.99% K$_2$PdCl$_4$ | 0.63 (0.58) | 0.52 (0.39) | 275 | 50 | 140 | 94.6 | 220 |
| | | | | | | 150 | 93.0 | 280 |
| | | | | | | 160 | 90.6 | 365 |
| 11b. (SMS) | 99.99% K$_2$PdCl$_4$ | 0.63 (0.58) | 0.52 (0.39) | 300 | 50 | 140 | 94.1 | 235 |
| | | | | | | 150 | 92.9 | 310 |
| | | | | | | 160 | 90.4 | 405 |
| 11c. (SMS) | 99.99% K$_2$PdCl$_4$ | 0.63 (0.58) | 0.52 (0.39) | 325 | 50 | 140 | 94.4 | 120 |
| | | | | | | 150 | 92.9 | 184 |
| | | | | | | 160 | 90.4 | 278 |
| 12. (SMS) | 99.99% K$_2$PdCl$_4$ | 0.96 (NA) | 0.76 (NA) | 300 | 50 | 140 | 91.6 | 211 |
| | | | | | | 150 | 89.5 | 319 |
| | | | | | | 160 | 83.4 | 420 |
| 13. (SMS) | 99.99% K$_2$PdCl$_4$ | 0.63 (0.58) | 0.52 (0.34) | 299°C.H$_2$ 10 minutes | 50 | 150 | 92.3 | 430 |
| | | | | 15 minutes | | 150 | 91.7 | 412 |
| | | | | 30 minutes | | 150 | 91.5 | 394 |
| | | | | 1 hour | | 150 | 91.4 | 420 |
| | | | | 5 hour | | 150 | 90.9 | 420 |

[1]In the first column, the fixing agent used is denoted as SMS, NaOH, or KOH and represent sodium metasilicate, sodium hydroxide, and potassium hydroxide, respectively.
[2]In the third and fourth column the targeted palladium and gold level are given while the numbers in parentheses are measured palladium and gold by ICP analysis.

Examples 1–5 show that good VA catalyst can be made using sodium metasilicate, sodium hydroxide or potassium hydroxide as the fixing agent. The source of the gold used was ACS grade hydrogen tetrachloroaurate (III) trihydrate form Aldrich and it was used in all the examples (1–13). The source of the palladium was varied. Examples 3–5 show that high purity (99.99%) K$_2$PdCl$_4$ gives higher space time yield than the lower purity (99%) K$_2$PdCl$_4$ shown in example 2 and high purity Na$_2$PdCl$_4$ shown in Example 1.

Examples 5 and 5a show the benefits of reducing the catalyst at 300° C. compared to 150° C. when sodium hydroxide is used as the fixing agent and (99.99%) K$_2$PdCl$_4$ is used as the palladium source. In these examples one batch of impregnated support was made and split into two portions for reduction at the two reduction temperatures. The catalyst in Example 5a with the 300° C. reduction shows increased space time yield. At 160° C. reaction temperature, the advantage is about 5%. However at the lower operating temperature of 140° C., the advantage is over 18%.

Examples 6, 7 and 7a were identically made with lower purity (98%) Na$_2$PdCl$_4$ using sodium metasilicate as the fixing agent. The difference was the impregnated support was reduced with ethylene at 150°, 300°, and 500° C., respectively. These examples show that even with a lower purity sodium source, a large improvement in space time yield is obtained by reducing at 300° C. compared to 150° C. However, when impregnated support was reduced at 500° C., activity was reduced to 0.

Examples 8, 8a, 9, 9a show the results of catalysts evaluated at two reaction pressures, 120 and 50 psig. In examples 8 and 9 at 120 psig, the space time yield is about twice that of examples 8a and 9a run at 50 psig and a reaction temperature of 140° or 150° C. Example 8 with high gold loading is a case where mass transfer limitations at 120 psig and 160° C. reaction temperature provide only a marginal increase (12%) in space time yield. In the remaining examples, reaction pressure was maintained at 50 psig to circumvent this mass transport problem in the lab.

Examples 10, 10a, 10b show the results using catalyst prepared with sodium metasilicate as the fixing agent and high purity (99.99%) K$_2$PdCl$_4$ as the palladium source. Ethylene reduction at 300° C. results in a catalyst producing VA at 20–40% higher space time yield compared to catalyst reduced at 150° C. Example 10b shows that with 350° C. reduction with ethylene the activity is greatly diminished.

Examples 11, 11a, 11b, 11c show the results of catalyst identically prepared except the ethylene reduction temperature varied from 150° to 325° C. The best performing catalyst is the one synthesized from impregnated support reduced near 300° C.

Example 12 is a catalyst in which both the palladium and gold loading were raised to targeted values of 0.96 and 0.76%, respectively and the ethylene reduction temperature was 300° C. Space time yields were good but selectivity to VA is lower compared to example 11b.

Example 13 shows performance of a catalyst formed from impregnated support reduced in hydrogen (5% H$_2$ in nitrogen) at 299° C. for different time.

Although particular embodiments of the invention have been described in detail for purposes of illustration, various modifications may be made without departing from the spirit and scope of the invention as defined by the appended claims.

What is claimed is:

1. A process for producing a catalyst, which catalyzes a reaction of an alkene, an alkanoic acid and an oxygen-containing gas to produce an alkenyl alkanoate, that comprises support particles impregnated with palladium, gold and a potassium alkanoate, said process comprising the steps of:

(a) impregnating the support particles with aqueous solutions of water-soluble palladium and gold compounds;

(b) precipitating water-insoluble palladium and gold compounds onto the support particles from solutions using alkali metal silicates or hydroxides as a precipitating agent;

(c) washing the precipitated support with water until a decant of said wash water is negative to a silver nitrate test;

(d) drying the washed precipitated support;

(e) converting the precipitated water-insoluble palladium and gold compounds to palladium and gold on the support particles using ethylene as a reducing agent at a temperature of greater than 150° C. up to 310° C. or hydrogen as a reducing agent at a temperature of greater than 150° C. up to 299° C.;

(f) further impregnating the support particles with said potassium alkanoate to a point of incipient wetness of the support particles; and (g) drying the catalyst.

2. The process of claim 1, wherein the catalyst carries from 1.0 to 4.5 wt. % potassium.

3. The process of claim 2, wherein the catalyst is reduced ethylene at a temperature of 200° C. to 310° C.

4. The process of claim 2, wherein the catalyst is reduced with hydrogen at a temperature of 200° C. to 299° C.

5. A process for producing a catalyst, which catalyzes a reaction of an ethylene, an acetic acid and an oxygen-containing gas to produce vinyl acetate, that comprises support particles impregnated with palladium, gold and potassium acetate, said process comprising the steps of:

(a) impregnating the support particles with aqueous solutions of palladium and gold salts and acids;

(b) precipitating water-insoluble palladium and gold compounds onto the support particles from such solutions using alkali metal metasilicates or alkali metal hydroxides or mixtures thereof as a precipitating agent;

(c) washing the precipitated support with water until a decant of said wash water is negative to a silver nitrate test;

(d) drying the washed precipitated support;

(e) converting the precipitated water-insoluble palladium and gold compounds to palladium and gold on the support particles using ethylene as a reducing agent at a temperature of greater than 150° C. up to 310° C. or hydrogen as a reducing agent at a temperature of greater than 150° C. up to 299° C.;

(f) further impregnating the support particles with potassium acetate; and (g) drying the catalyst.

6. The process of claim 5, wherein the potassium tetrachlorpalladate is of 99.99% purity.

7. The process of claim 6, wherein the hydrogentetrachloraurate is of 99.998% purity.

8. The process of claim 7, wherein the catalyst carries from 0.5 to 1.2 wt. % Pd.

9. The process of claim 8, wherein the catalyst carries from 0.3 to 2.4 wt. % Au.

10. The process of claim 9, wherein the catalyst carries from 1.0 to 4.5 wt. % potassium.

11. The process of claim 10, wherein the impregnated support is reduced with ethylene at a temperature of 250° C. to 310° C.

12. The process of claim 10, wherein the catalyst is reduced with hydrogen at a temperature of 200° C. to 299° C.

13. A process for production of vinyl acetate at a space time yield value of at least 300 g VA/L cat/ hr at 50 psig and 600 g VA/L cat/ hr at 120 psig by a catalyzed gas phase reaction of a reactive gas composition comprising ethylene, an acetic acid and an oxygen, comprising the steps of (a) passing the reactive gas composition into contact with a catalyst produced by (1) impregnating support particles with aqueous solutions of palladium and gold salts and acids;

(2) precipitating water-insoluble palladium and gold compounds onto the support particles from such solutions using alkali metal metasilicates or alkali metal hydroxides or mixtures thereof as a precipitating agent;

(3) washing the precipitated support with water until a decant of said wash water is negative to a silver nitrate test;

(4) drying the washed precipitated support;

(5) converting the precipitated water-insoluble palladium and gold compounds to palladium and gold on the support particles using ethylene as a reducing agent at a temperature of greater than 150° C. up to 310° C. or hydrogen as a reducing agent at a temperature of greater than 150° C. up to 299° C.;

(6) further impregnating the support particles with potassium acetate; and (7) drying the catalyst; and (b) maintaining the reactive gas composition at a temperature of or less than 160° C.

14. The process of claim 13, wherein the palladium salt is potassium tetrachlorpalladate of 99.99% purity.

15. The process of claim 14, wherein the gold acid is hydrogentetrachloraurate of 99.998% purity.

16. The process of claim 15, wherein the catalyst carries from 0.5 to 1.2 wt. % Pd.

17. The process of claim 16, wherein the catalyst carries from 0.3 to 2.4 wt. % Au.

18. The process of claim 17, wherein the catalyst carries from 1.0 to 4.5 wt. % potassium.

19. The process of claim 18, wherein the catalyst is reduced with ethylene at temperature of 250° C. to 310° C.

20. The process of claim 19, wherein the catalyst is reduced with hydrogen at a temperature of 200° C. to 299° C.

21. The process of claim 13, wherein prior to step (5) and after step (4) the precipitated support is treated in a flow of an inert gas at 150° C. for 0.5 to 1 hour and then heated to 300° C.

* * * * *